United States Patent [19]

Bäckerud

[11] Patent Number: 5,337,799
[45] Date of Patent: Aug. 16, 1994

[54] METHOD FOR THE PRODUCTION OF COMPACTED GRAPHITE CAST IRON

[75] Inventor: Stig L. Bäckerud, Bloomfield Hill, Minn.

[73] Assignee: Sintercast AB, Stockholm, Sweden

[21] Appl. No.: 39,412

[22] PCT Filed: Oct. 11, 1991

[86] PCT No.: PCT/SE91/00685

§ 371 Date: Apr. 15, 1993

§ 102(e) Date: Apr. 15, 1993

[87] PCT Pub. No.: WO92/06809

PCT Pub. Date: Apr. 30, 1992

[51] Int. Cl.$^5$ .................. B22D 2/00; C21C 1/10; G01N 25/04
[52] U.S. Cl. .................. 164/4.1; 164/58.1; 75/377; 374/26
[58] Field of Search .......... 164/4.1, 150, , 154, 164/58.1; 374/26; 75/377; 266/79, 99

[56] References Cited

U.S. PATENT DOCUMENTS

| | | | |
|---|---|---|---|
| 4,046,509 | 9/1977 | Bäckerud | 164/4.1 |
| 4,059,996 | 11/1977 | Cure | 73/354 |
| 4,261,740 | 4/1981 | Plessers | 75/129 |
| 4,333,512 | 6/1982 | Sugiura et al. | 164/150 |
| 4,354,391 | 10/1982 | Li | 164/4.1 |
| 4,358,948 | 11/1982 | Plessers | 374/26 |
| 4,667,725 | 5/1987 | Backerud | 164/4.1 |
| 4,696,337 | 9/1987 | Grochal et al. | 164/150 |
| 4,765,391 | 8/1988 | Backerud | 164/150 |

FOREIGN PATENT DOCUMENTS

| | | | |
|---|---|---|---|
| 0157308 | 3/1985 | European Pat. Off. . | |
| 0287391 | 2/1991 | Fed. Rep. of Germany | 164/4.1 |
| 3101050 | 5/1988 | Japan | 164/4.1 |
| 0530002 | 12/1972 | Switzerland . | |

Primary Examiner—P. Austin Bradley
Assistant Examiner—Erik R. Puknys
Attorney, Agent, or Firm—Cushman, Darby & Cushman

[57] ABSTRACT

A method relating to the production of cast iron castings with compacted graphite crystals. The method comprises controlling and correcting the composition of the cast iron melt and securing the necessary amount of structure modifying agent. A sample of the melt is taken with a sample vessel provided with two thermocouples, one positioned so as to be in the centre of the sample and the other positioned so as to be in the vicinity of the vessel wall. The vessel wall contains or is coated with a layer of a substance which will lower the concentration of dissolved elementary magnesium in the melt in the vicinity of the vessel wall by at least 0.0030%. The temperature/time values obtained through two temperature responsive means are recorded. The occurrence of a plateau temperature will provide information as to the precipitation of flaky graphite in the vicinity of the vessel wall, therewith enabling corrections to be made to the concentration of the modifying agent and to ensure the formation of compacted graphite crystal during the whole of the pouring time required in the foundry process concerned.

6 Claims, 1 Drawing Sheet

METHOD FOR THE PRODUCTION OF COMPACTED GRAPHITE CAST IRON

BACKGROUND OF THE INVENTION

The present invention relates to a method for the production of compacted graphite cast iron. The method is based on a test-method to determine the structural characteristics of a melt for casting compacted graphite cast iron and means to control the structure and properties of the material produced.

U.S. Pat. No. 4 667 725 describes a method for producing castings with a predetermined graphite structure. The method comprises taking a sample from a bath of molten iron and then allowing the sample to solidify over a period of from 0.5 to 10 minutes. During the solidification period, recordings are made of the temperature changes that take place in the centre of the sample volume and near the inner wall of the sample vessel. The sample vessel should substantially be in thermal equilibrium at a temperature above the crystallization temperature of the bath and be allowed to solidify fully over a period of from 0.5 to 10 minutes. The temperature-time sequence is is measured by two temperature responsive means, of which one is placed in the centre of the sample quantity and the other in the molten material at a location close to the wall of the vessel. The degree of dispersion of the graphite phase in relation to known reference values for the same sampling and testing process with respect to finished castings is assayed with the aid of the temperature measured during the first nucleation events of the eutectic reaction measured at said vessel wall as the minimum undercooling temperature at the vessel wall, the recalescence of the vessel wall, the positive difference between the temperature that prevails at the vessel wall and in the centre of the sample and the derivative of the temperature decrease at said vessel wall during the time for constant eutectic growth temperature in the centre of the sample quantity, alternatively the highest negative values of the temperature difference between the eutectic maximum growth temperature and the eutectic temperature. If the bath has an insufficiency of crystallization nuclei, a graphite nucleating agent is introduced thereinto and conversely when the crystallization nucleants are present in excess the degree of dispersion is lowered by holding the bath for a length of time sufficient to reduce the amount of nuclei in the bath prior to casting, by assessing the morphology of the graphite precipitation in relation to corresponding data obtained with the same sampling and testing technique as that applied with cast iron of known structure, with the aid of supercooling that takes place in the centre of the molten material, the recalescence in the centre of the sample vessel and the maximum growth temperature, and by correcting the quantity of structure-modifying agent in response thereto, so that graphite precipitation takes place in a predetermined form upon solidification of the molten cast iron subsequent to casting. The obtained values are used to determine the amount of modifying agent and the presence of graphite nucleating agent in the melt concerned and for the equipment used. The production equipment used has to be calibrated and possibly necessary additions of modifying element and nucleating agent have to be made in relation to the calibration of the best equipment.

The above-mentioned method permits the skilled person to predict how the graphite precipitation will take place in the melt concerned and also how to control the composition of the melt to obtain desired results. The test method gives results which cannot be obtained with other analysis methods. Although a chemical test will, for instance, disclose the total amount of magnesium present, it will provide no information as to how much magnesium there is in solution and thus active as a modifying agent. This latter information is of great importance since the amount of magnesium in solution in an iron melt will change relatively quickly due to physical and chemical reactions that take place within the melt and due to contact with the surroundings and consequently although a conventional chemical analysis may have given the correct results in respect of the melt concerned at the time of making the analysis may well have changed its status at the time of receiving the analysis results to such an extent that this result can no longer be used to control the solidification process, when casting cast iron objects.

The amount of dissolved elemental magnesium is essential for controlling the graphite precipitation- In addition to magnesium or instead of magnesium the structure modifying agent can contain cerium and other rare earth metals. The modifying agent (and the nucleating agent) will fade with time and there are characteristic rates for this fading, contingent on the process and equipment used. A good control method will enable an exact determination to be made of the amount of modifying and inoculating agents present and will also enable a calculation to be made as to how much of these agents are needed to obtain acceptable results for a casting process during the following say 10 to minutes. This has not, however, been possible hitherto. The method described earlier can only inform us that the melt at the sample extraction moment will solidify with specific graphite crystal form.

The undercooling in a melt where flaky graphite crystals develop is relatively small (<5° C.) and the minimum represents the situation where a certain number of graphite crystals (together with the austenite phase) have attained a growth rate at which the latent heat evolved balances the heat extracted from the system. After this point, the liquid melt is actually heating up to a new balance point representing the "steady state growth condition", which in the case of a well nucleated liquid with A-graphite is close to the equilibrium temperature $T_E$ say 1°-2° C. below the equilibrium temperature of the eutectic reaction in normal Fe-C-Si-alloys. In the present document, the equilibrium temperature is set at 1155° C. This means that the instruments have been calibrated to a $T_E = 1155°$ C. and temperature differences calculated in relation therewith. Thermodynamic calculations in the literature give other, somewhat higher vlaues, but for practical reasons $T_E$ is in this connection set at 1155° C.

If modifying agents such as magnesium and rare earth metals are added and dissolved in a liquid cast iron melt, the growth in specific crystallographic directions is restricted and the morphology changed from flaky via compacted to nodular graphite crystals with increasing amounts. From type IV to I in the graphite classification scale.

If there are sufficient graphite precipitation nuclei present and a proper amount of modifying elements is present, the cast iron will solidify as compact graphite cast iron. In this case, the undercooling is much higher than is observed for gray iron before the rare of growth of compacted graphite crystals generates enough heat to counteract and heat-extraction from the system.

The reheating (recalescence) takes a longer time, due to growth restrictions, and the steady state growth temperature will stay from 5° to 10° C. below the equilibrium liquidus temperature, $T_E$.

The relationship between the growth habit of these two graphite morphologies and the thermal analysis results and curves have long been known.

The successive change in morphology from flaky to compacted graphite as a result of increasing additions of modifying elements is, however, of interest because of its great importance in enabling thermal analysis to be used as a process control instrument.

This change is by no means a linear function of the concentration of modifying additives, for the following reasons:

Here, magnesium is referred as an example of the modifying agent used and when adding a modifying agent, the magnesium will react with any sulphur and oxygen that may be present while forming MgS and MgO. The remainder of the magnesium will dissolve in the cast iron melt and is defined as $Mg_{(L)}$.

In a set of experiments, it has been found that a $Mg_{(L)}$-level of 0,008% Mg will give a fully compacted graphite structure and an $Mg_{(L)}$-level below 0.006% Mg will give a fully flaky structure in a slightly hypoeutectic cast iron (the carbon equivalent CE of 4.0-4.2). A level of dissolved magnesium below 0.006% will not be sufficient to prevent the formation of flaky graphite. This formation will release latent heat at such a high rate as to reduce the degree of undercooling, and the growth of compacted graphite crystals is never triggered. At this lower degree of undercooling, some crystals may, however, be influenced by the modifying agent to such an extent that they develop in a somewhat unspecified modified form.

Compacted graphite crystals are formed in the range between 0,008-0,016% dissolved magnesium. No flaky crystals are formed in this range, but towards the higher end of this range a certain formation of nodular crystals can be observed.

The absolute values of the content of dissolved elemental magnesium may vary from one foundry to another and with constituents in the base melt, but in one actual case the following figures were obtained, which may serve as an example:

0–0.008% Mg, flaky graphite
0.008–0.016% Mg, compacted graphite
0,016–0.030% Mg, mix of compacted and nodular graphite
0,030–0.035% Mg, 80–100% nodular graphite
>0.035% Mg, fully nodular graphite (Mg in excess)

From one practical application, it was found that for the process and equipment used, the fading of magnesium was about 0.001% Mg every five minutes. During a casting period of 15 minutes, the content of dissolved elemental magnesium thus decreased with 0.003%. If the original percentage was 0.010% Mg, one would obtain after 15 minutes a content of 0.007% and a large portion of flaky graphite will thus be formed by the end of the casting period, while a sample that originally contains say 0.012% Mg will form only compacted graphite crystals over the whole casting period. If the melt had been tested according to U.S. Pat. No. 4,667,725, it would have been found in both cases, quite correctly, that both melts would solidify as compacted graphite cast iron. The method does not permit a discrimination to be made between magnesium contents of 0.010% and 0.012%. As graphite flakes have to be completely avoided, it has so far been necessary to use a certain excess of magnesium in order to secure a desired result, with the risk of obtaining a certain amount of nodular graphite crystals in the material being produced.

The decrease of the content of dissolved elementary magnesium below about 0.008% will result in a very rapid increase of the amount of flaky graphite due to the fact that an insufficient amount of magnesium permits the growth of flakes of graphite and that a decrease of the magnesium content below the borderline will result in a drastic transformation of the solidification structure with regard to the graphite precipitation. This will be obvious from the Figure, where the amount of compacted graphite and flaky graphite is shown along the ordinate and the percentage of dissolved magnesium along the abscissa. The curve shows the drastic change that occurs, when the magnesium content drops below 0.008% magnesium. Other modifying agents have similar threshhold concentrations.

Once the growth habit of the graphite crystals if fully compacted, the test will result in mutually identical signals from the analysis equipment within the range concerned, i.e. between 0,008-0.16% $Mg_{(L)}$. A chemical analysis is not useful since there is no fast method known of discriminating between total and dissolved magnesium quantities.

SUMMARY OF THE INVENTION

According to the present invention, compacted graphite iron can be produced consistently.

Thus, a melt of suitable composition and structure is prepared and a modifying and nucleating agent is added to the melt in an amount which is expected to be sufficient to produce compacted graphite cast iron. A sample is then extracted from the melt in a sample vessel, the wall of which contains or is covered on its inside surface with a layer consisting of a material which will react with dissolved elementary magnesium present in the vicinity of said wall. The layer material or the wall constituents should be present in such amounts that the magnesium concentration of the sample melt in the vicinity of the wall will be lowered by 0.003%. The sample vessel must have two thermocouples, one placed in the centre of the melt amount and the other in the vicinity of the vessel wall. The temperatures are recorded both from thermocouples and the general information is used in accordance with the teachings of U.S. Pat. No. 4,667,725. When the magnesium content is as low as about 0.010%, the curve obtained from the thermocouple placed in the vicinity of the vessel wall will show a level of temperature at which precipitation of flaky graphite occurs, since the local Mg-content is <0,008% Mg. This is an indication that the magnesium content has to be adjusted by adding magnesium. This can be done by adding further structure modifying agent to the melt, such as to compensate for the fading loss of structure modifying agent during the whole of the casting operation. Normally, this addition can be made without any further control of the solidification properties, which also permits the structure modifying agent to be added directly when casting.

In a practical embodiment of the present invention, the sampling vessel is produced from oxides which react with the modifying agent, i.e. magnesium, in the cast iron melt. The vessel can be made of a mixture of aluminium oxide and the chamotte. The reaction rate determining compounds in such a material are silicon dioxide, small amounts of alkali metal oxides and the sulphur impurity level. The more stable oxides, such as aluminium oxide and calcium oxide, are not likely to take part in the magnesium reduction process during the short contact period between melt and crucible.

One example of commercial products which can be used for the production of sample vessels useful when practicing the present invention is 50% SECAR® 71, (Lafarge S.A.) which mainly consists of a 71% $Al_2O_3$, 27% CaO and less than 2% total impurities, among which 0.35% $SiO_2$, 0.35% $Na_2O$, 0.25% $Fe_3O_3$, 0.05% $H_2O$ and 0.15% $SO_3$ can be mentioned, and 50% Refag (Alfa Aggregates Ltd., Newcastle), mainly consisting of 52% $SiO_2$, 41.5% $Al_2O_3$, 3% $Fe_2O_3$, 0.5% $K_2O$ and 0.1% $Na_2O$.

It will be understood that both sampling temperature and the time lapse between sampling and the start of solidification (=liquid cooling rate) plays a part establishing the desired concentration profile.

The method of the present invention results in an increased yield of acceptable castings. The method, according to U.S. Pat. No. 4,667,725, gives in one practical case about 90% acceptable castings, i.e. with more than 80% compacted graphite. According to the present invention, these figures have been increased in practice to above 99.5%.

BRIEF DESCRIPTION OF THE DRAWINGS

The invention will now be explained in more detail with reference to the Figures.

DETAILED DESCRIPTION

Figure 1:
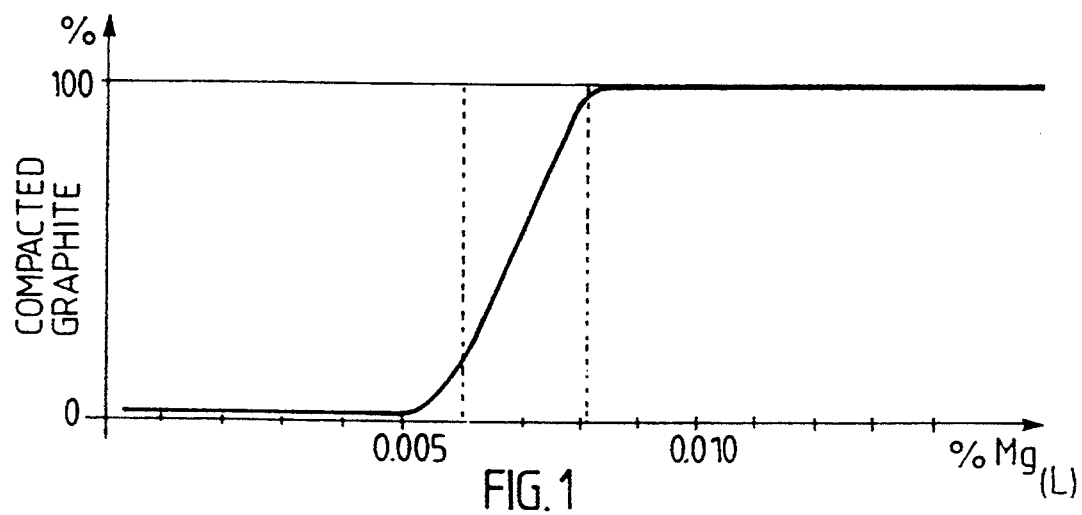
FIG. 1 is a diagram, which shows the percentage graphite in compacted form with the remainder being flaky graphite and from which it will be seen that above about 0.008% $Mg_{(L)}$ the graphite is fully compacted and below about 0.006% is almost fully flaky. Between 0 006% and 0.008% $Mg_{(L)}$, there exists a sharp transition region with different proportions of the two graphite structures.
Figure 2:
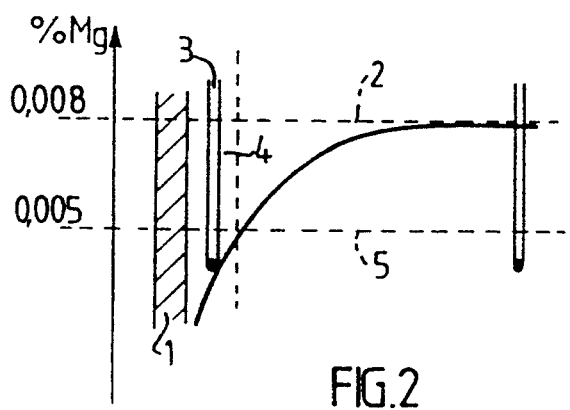
FIG. 2 is a diagram inserted in a schematic illustration of a sample vessel and defining the percentage of dissolved magnesium in the sample vessel from the vessel wall towards the centre of the sample vessel. The sample vessel wall is indicated on the left of the Figure and an assumed level of dissolved $Mg_{(L)}$ in the centre is indicated by a dotted horizontal line (0.008 $Mg_{(L)}$. The $Mg_{(L)}$ level at a thermocouple in the vicinity of the sample wall is indicated by another dotted line 5 (0.005% $Mg_{(L)}$). The region where flaky graphite crystals are formed is indicated by the area 4.
Figure 3:
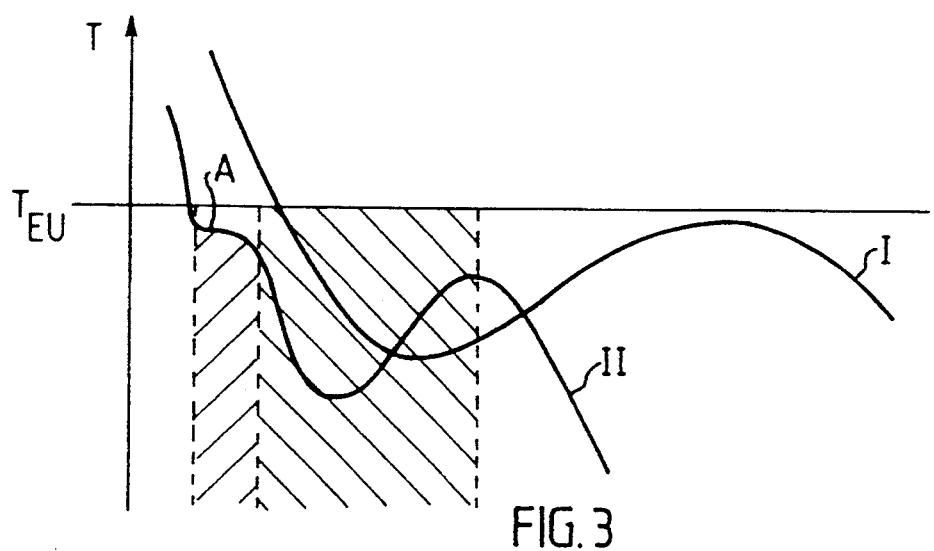
FIG. 3 shows the temperature/time curves for a thermocouple in the centre I and the thermocouple in the vicinity of the sample vessel wall II. Curve I is a typical curve for the compacted graphite solidification in the centre of the sample. Curve II shows at A an inflexion which is typical of a flaky graphite solidification. The relative stay time on the first plateau (A) is proportional in relation to the amount of flakes in the area in the vicinity of the sample wall.

The following example elucidates the invention. The example assumes that there is used a production line in which the Mg fading rate is estimated to be 0.001% Mg for each 5 minutes and that the last moulds in said line are filled with melt about 15 minutes after the sample was taken.

EXAMPLE

Production of compacted graphite cast iron. The true Mg-level at the moment of sampling was 0.010% of free, dissolved elementary magnesium. A thermal analysis made from the centre of the sample showed that the melt will result in a substantially compacted graphite material, while the termocouple in the vicinity of the wall showed a tendency towards flake formation. The information thus obtained indicated that the remaining Mg-level would be reduced to 0,008% after a time period about 10 minutes and that the last third of the castings would contain graphite in flaky form, provided that the Mg-level was not increased. The need for additional amounts of magnesium was obvious from the temperature-time-curve obtained from a thermocouple located in the vicinity of the vessel wall.

This structure prediction cannot be achieved with the method known from U.S. Pat. No. 4,667,725.

I claim:

1. A method for producing compacted graphite cast iron castings, comprising:
   (a) providing a melt of molten iron;
   (b) adding to said melt a magnesium-containing modifying and nucleating agent in an amount which is nominally sufficient to cause said melt upon solidification to produce compacted graphite cast iron;
   (c) extracting a sample from the melt to which said agent has been added, into a sample vessel having an internal surface layer in contact with said sample which is capable of reacting with magnesium contained in said sample so as to decrease concentration of dissolved magnesium in said sample adjacent said internal surface layer by a predetermined percent by weight of said sample, said predetermined percent being substantially the same percent by which dissolved magnesium will fade and become effectively unavailable to cause production of compacted graphite cast iron structure in castings to be made by pouring quantities of the melt into a succession of molds over a given period of time;
   (d) sensing temperature of said sample at a first site located centrally of said sample and at a second site adjacent said internal surface as the sample solidifies, and, from analyzing resulting temperature versus time profiles from said sites determining whether said sample has solidified into a given percentage of compacted graphite cast iron structure at both of said sites; and
   (e) upon determining from practicing step (d) that the sample, at said second site thereof, has solidified to provide a percentage of compacted graphite, which is less than said given percentage,
      (i) adding an additional quantity of said agent to said melt, and then
      (ii) pouring said melt and permitting the poured melt to solidify into a succession of iron castings of which more than 90 percent have at least said given percentage of compacted graphite cast iron structure.

2. The method of claim 1, wherein:
said predetermined percent is 0.003 percent, and said given period of time is about 15 minutes.

3. The method of claim 1, wherein:
step (d) is performed using respective thermocouples as temperature sensors at said first and second sites.

4. The method of claim 1, wherein:

said internal surface layer of said sample vessel is made of at least 10 percent by weight of at least one oxide selected from the group consisting of silicon, manganese and iron oxides.

5. The method of claim 1 wherein:
said internal surface layer of said sample vessel is made of at least 0.5 percent by weight of at least one oxide selected from the group consisting of potassium and sodium oxides.

6. The method of claim 1, wherein:
said lateral surface layer of said sample vessel is made of cement and ballast material together containing 10–30 percent $SiO_2$, by weight.

* * * * *